United States Patent
Thiele

(10) Patent No.: US 6,372,924 B2
(45) Date of Patent: *Apr. 16, 2002

(54) PROCESS FOR THE PREPARATION OF EPOXIDES FROM OLEFINS

(75) Inventor: Georg Thiele, Hanua (DE)

(73) Assignee: Degussa-Huls AG, Frankfurt am Main (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/663,703

(22) Filed: Sep. 18, 2000

(30) Foreign Application Priority Data

Sep. 18, 1999 (DE) .......... 199 44 839

(51) Int. Cl.$^7$ .......... C07D 301/12
(52) U.S. Cl. .......... 549/531
(58) Field of Search .......... 549/531

(56) References Cited

U.S. PATENT DOCUMENTS

| | | | |
|---|---|---|---|
| 4,476,327 A | 10/1984 | Neri et al. | |
| 4,937,216 A | 6/1990 | Clerici et al. | |
| 5,412,122 A | 5/1995 | Saxton et al. | |
| 5,912,367 A | * 6/1999 | Chang | .......... 549/529 |

FOREIGN PATENT DOCUMENTS

| | | |
|---|---|---|
| EP | 100 118 | 10/1985 |
| EP | 230 949 | 7/1992 |
| EP | 795 537 | 9/1997 |
| WO | WO 99/48882 | 9/1999 |

OTHER PUBLICATIONS

Clerici, M. et al., "Expoxidation of Lower Olefins with Hydrogen Peroxide and Titanium Silicalite", Journal of Catalysts, U.S. Academic Press, Duluth, MN, Bd. 140, Nr. 1, Mar. 1993, pp. 71–83.

Gao, H. et al., "Expoxidation of allyl chloride with hydrogen peroxide catalyzed by titanium silicalite 1," Appl. Catal. A 138 (1996) pp. 27–28.

* cited by examiner

Primary Examiner—Joseph K. McKane
Assistant Examiner—Joseph Murray
(74) Attorney, Agent, or Firm—Pillsbury Winthrop LLP

(57) ABSTRACT

A process for the preparation of epoxides by epoxidation of olefinic compounds with hydrogen peroxide in the presence of a titanium silicalite as a catalyst. A base is introduced into the epoxidation reactor directly or as a mixture with one or more starting substances, under pH control. A pH in the range from 4 to 9.5, preferably a pH of 5 to 9.5, is established and maintained in the reaction mixture or in the starting substance containing the base. Preferably, an aqueous-organic hydrogen peroxide solution with a pH in the range from 8 to 9 is employed and the epoxidation is carried out in a fixed bed reactor.

8 Claims, No Drawings

PROCESS FOR THE PREPARATION OF EPOXIDES FROM OLEFINS

CROSS-REFERENCE TO RELATED APPLICATION

This application is based on German Application DE 199 44 839.6, filed Sep. 18, 1999, which disclosure is incorporated herein by reference.

FIELD OF THE INVENTION

The invention relates to a process for the preparation of epoxides by epoxidation of olefinic compounds with hydrogen peroxide in the presence of a titanium silicalite as a catalyst.

BACKGROUND OF THE INVENTION

It is known from EP-B 0 100 118 that olefins can be epoxidized with hydrogen peroxide and converted to glycol ethers in situ in the presence of alcohols if a titanium-containing zeolite, such as a titanium silicalite, is employed as a catalyst. In respect of the preparation of epoxides, the acid properties of this catalyst are a disadvantage, because some of the epoxide formed reacts further during the reaction by acid-catalyzed ring-opening to give the diol or, in the presence of an alcohol as the solvent, to give diol ethers.

It is known from EP 0 230 949 that the epoxide ring-opening reaction can be partly suppressed if the catalyst is neutralized with a neutralizing agent before and/or during the epoxidation reaction. Strong bases, such as NaOH and KOH, and weak bases, such as ammonia, alkali metal carbonates, alkali metal bicarbonates and alkali metal carboxylates, are mentioned as neutralizing agents. This document indeed imparts a doctrine for the treatment of the catalyst with a base before the epoxidation, but it gives no suggestion as to how the catalyst is to be neutralized during the epoxidation.

M. G. Clerici and P. Ingallina describe in J. Catal. 140 (1993) 71–83, a process of this type and the influence of acids, bases and salts on the catalytic activity of the titanium silicalite catalyst. According to this paper, it is known that the effect of a neutralizing agent on the catalytic properties depends greatly on the amount of neutralizing agent. While the use of a small amount of the neutralizing agent leads to an increase in the selectivity, if the amount is too large there is an inhibition of the catalytic activity for the epoxidation, up to complete blocking of the activity of the catalyst. It is furthermore known that acids present in the reaction medium can increase the rate of reaction. It is known from H. Gao, G. Lu, J. Suo, S. Li, Appl. Catal. A 138 (1996) 27–38, that this adverse effect of the neutralizing agent occurs even at low concentrations, and that concentrations of NaOH or KOH of less than 600 ppm can lead to a severe loss in catalytic activity.

The known process for the epoxidation of olefins with hydrogen peroxide and a titanium silicalite catalyst with the addition of basic substances has the disadvantage that, to date, the amount of neutralizing agent required for the desired effect of improving the selectivity and at the same time not reducing or only moderately reducing the rate of reaction, cannot be determined in advance for an individual case. For carrying out the reaction in practice, this has the disadvantage that, if a neutralizing agent is used, a small change in the quality of the starting substances and/or the properties of the catalyst can lead to a marked and unforeseeable change in the activity of the catalyst during the epoxidation. The abovementioned documents give no suggestion as to how the amount of base to be added to the system can be controlled within narrow limits.

SUMMARY OF THE INVENTION

The object of the present invention is to provide a process for the preparation of epoxides from olefins in which the disadvantages described above for the process can be overcome. The present process allows either discontinuous or, preferably, continuous operation. The invention allows the process to be carried out such that, with the highest possible increase in selectivity, the conversion proceeds in a manner which can be determined in advance.

It has been found, surprisingly, that the object can be achieved in that the addition of the base to the epoxidation reactor is carried out with monitoring of the pH and the amount of base is chosen such that for the hydrogen peroxide employed or the mixture of hydrogen peroxide with one or more solvents employed, a constant pH can be determined beforehand by the results of one or more test experiments.

The invention thus provides a process for the preparation of an epoxide, comprising epoxidation of an olefinic compound with hydrogen peroxide in the presence of a titanium silicalite catalyst. A solution containing hydrogen peroxide and the olefinic compound are introduced as starting substances periodically or continuously into an epoxidation reactor and a base is additionally employed in the process. The base is introduced into the epoxidation reactor directly or in a mixture with one or more of the starting substances, while controlling the pH. The pH control is carried out in the reaction mixture or in the mixture(s) of the base and starting material(s). A pH in the range from 4 to 9.5 is established and kept substantially constant. Since the pH in the reaction mixture decisively influences the selectivity and the conversion, the optimum pH is determined beforehand by one or more epoxidation test experiments carried out at different pH values using the same starting substances, with subsequent determination of the selectivity and the conversion.

By choice of a suitable constant pH, the epoxide selectivity in the epoxidation of olefins with hydrogen peroxide with a titanium silicalite catalyst can be improved in a reproducible manner, while at the same time the activity of the catalyst decreases only slightly and in a reproducible manner. If a constant pH is established, variations in the quality of the starting substance or in the composition of the catalyst have less effect on the course of the reaction than if a constant amount of the neutralizing agent is added.

According to a preferred embodiment, the base is added to an aqueous or aqueous-organic hydrogen peroxide solution and the optimum pH, determined from preliminary experiments, for example a pH-dependent test series, is established and kept constant in the solution obtained in this way. In the case of an aqueous hydrogen peroxide solution, the optimum pH is in the range from 4 to 6.5, and in the case of an organic-aqueous hydrogen peroxide solution with at least 50 wt. % of an organic water-soluble solvent, the optimum pH is in the range from 5 to 9.5, the pH being based on measurement by means of a glass electrode. A combined glass electrode with integrated Ag/AgCl reference electrode is preferably used.

The process according to the invention is suitable for the epoxidation of aliphatic, cycloaliphatic and aliphatic-aromatic olefinic compounds. Olefins having 3 to 8 carbon atoms are preferably employed, particularly propene and 1-butene. The olefinic compound can contain one or more functional groups, such as e.g. hydroxyl, halogen, alkoxy or carbalkoxy. For example, allyl chloride and allyl alcohol can be readily epoxidized in the process according to the invention.

The hydrogen peroxide is employed in the process according to the invention in the form of an aqueous solution with a hydrogen peroxide content of 1 to 90 wt. %, preferably 10 to 70 wt. %, and particularly preferably 30 to 50 wt. %. The hydrogen peroxide can be employed in the form of commercially obtainable stabilized solutions. Non-stabilized aqueous hydrogen peroxide solutions, such as are obtained in the anthraquinone process for the preparation of hydrogen peroxide, are also suitable. As an alternative, hydrogen peroxide can also be used in an organic-aqueous solution or in an organic solution. Preferably, a pH-controlled aqueous or aqueous-organic hydrogen peroxide solution to which a base has been added is added to the epoxidation reactor.

Crystalline titanium-containing zeolites of the composition $(TiO_2)_x(SiO_2)_{1-x}$, where x is from 0.001 to 0.05, and an MFI or MEL crystal structure, known as titanium silicalite-1 and titanium silicalite-2, are particularly suitable as the catalyst. The titanium silicalite catalyst can be employed as a powder or as a shaped catalyst in the form of granules, extrudates or shaped bodies. For shaping, the catalyst can include 1 to 99% of a binder or support material. All binders and support materials which do not react with hydrogen peroxide or the epoxide under the reaction conditions used for the epoxidation are suitable. Granules according to EP-A 0 893 158 or extrudates with a diameter of 1 to 5 mm are preferably employed.

Suitable solvents are all the solvents which are not oxidized or are oxidized to only a small extent by hydrogen peroxide under the reaction conditions chosen and which dissolve in water to the extent of more than 10 wt. %. Solvents which are completely miscible with water are preferred. Suitable solvents are alcohols, such as e.g. methanol, ethanol or tert-butanol; glycols, such as e.g. ethylene glycol, 1,2-propanediol or 1,3-propanediol; cyclic ethers, such as e.g. tetrahydrofuran, dioxane or propylene oxide; glycol ethers, such as e.g. ethylene glycol monomethyl ether, ethylene glycol monoethyl ether, ethylene glycol monobutyl ether or the propylene glycol monomethyl ethers, and ketones, such as e.g. acetone or 2-butanone. Methanol is preferably added as the solvent. The weight ratio of hydrogen peroxide to organic solvent is preferably in the range from 1:1 to 1:20.

Bases which can be employed for the process according to the invention are all the substances by the addition of which the pH can be raised to the required value. Suitable bases are alkali metal hydroxides, ammonia, alkali metal carbonates, ammonium carbonate, alkali metal bicarbonates, ammonium bicarbonate and alkali metal and ammonium salts of carboxylic acids. Alkali metal and ammonium salts of polybasic mineral acids, such as e.g. phosphoric acid and pyrophosphoric acid, are also suitable. Aqueous solutions of the base are preferably employed, particularly preferably aqueous solutions of NaOH, LiOH or ammonia. According to another alternative, the base used to establish the pH is a buffer mixture, such as borax/HCl, borax/NaOH or $NaH_2PO_4$/NaOH.

All the physical parameters and measurement methods which give a measurement value which depends on the pH in a reproducible manner and varies with the pH are suitable for establishing the pH. A potentiometric measurement with a glass electrode which has a pH-dependent potential is preferably employed. Commercially available pH meters with which the potential is displayed directly on a scale in pH units and electrodes which give a stable and reproducible potential in aqueous hydrogen peroxide solutions or mixtures thereof with the solvent are suitable. Due to the content of hydrogen peroxide and optionally solvent, a concentration potential additionally occurs at the glass electrode, in addition to the pH-dependent potential. The pH measured with a commercially available pH instrument therefore deviates from the actual pH, i.e. the common logarithm of the hydrogen ion concentration, by a constant amount, the amount depending in a reproducible manner on the mixing ratio of water, hydrogen peroxide and optionally solvent. For aqueous hydrogen peroxide solutions, this deviation of the pH measurement with a glass electrode compared with the actual pH is known from J. R. Kolczynski, E. M. Roth, E. S. Shanley, J. Am. Chem. Soc. 79 (1957) 531–533.

The pH to be established to achieve the advantage according to the invention depends on the composition of the mixture of hydrogen peroxide, water and optionally solvent and can be determined, as the Examples below demonstrate, in a simple manner by a series of experiments in which the pH is varied. In the case of pH measurement with a glass electrode, the effect according to the invention on addition of the base to an aqueous hydrogen peroxide solution with a content of between 30 and 50 wt. % hydrogen peroxide is, as a rule, achieved when the pH is raised by 1 to 4 pH units and the pH displayed by the meter after addition of the base is between 4 and 6.5. In the same way, the effect according to the invention on addition of the base to a mixture of aqueous hydrogen peroxide and methanol is, as a rule, achieved when the pH is raised by 1 to 6 pH units and the pH displayed by the meter after addition of the base is between 5 and 9.5.

The process according to the invention for the epoxidation of olefins is carried out at a temperature of −10° to 100° C., preferably at 20° to 70° C. The olefin is preferably employed in excess with respect to the hydrogen peroxide, in order to achieve a substantial hydrogen peroxide conversion, the molar ratio of olefin to hydrogen peroxide being equal to or greater than 1; and preferably being in the range from 1.1 to 10. If an organic solvent is added, the amount of solvent is preferably chosen such that only one liquid phase is present in the reaction mixture. The solvent is preferably added in a weight ratio of 1 to 20 relative to the amount of hydrogen peroxide employed.

The amount of catalyst employed can be varied within wide limits and is preferably chosen such that under the reaction conditions applied, a hydrogen peroxide conversion of about 90%, preferably more than 95%, is achieved within 1 min to 5 h.

If an olefin with a boiling point under normal pressure below the reaction temperature chosen is reacted, the reaction is preferably carried out under pressure and under an atmosphere which substantially comprises the vaporous olefin; an olefin partial pressure in the range from 0.1 to 1 MPa is suitable. The pressure here is particularly preferably chosen between 50 and 100% of the saturation vapor pressure of the olefin at the reaction temperature.

In one embodiment of the invention, the catalyst is suspended in the reaction mixture during the epoxidation reaction. In this case the pH of the hydrogen peroxide or the mixture of hydrogen peroxide and solvent can optionally be established either before or after the addition of the catalyst. If the epoxidation reaction is carried out in a thoroughly mixed reactor, e.g. a stirred tank or a loop reactor, the pH measurement can optionally also take place in the reactor and the base for establishing the pH can be added directly to the reaction mixture.

In another preferred embodiment of the invention, the catalyst is employed in the form of a fixed bed or packing in a tubular reactor, as a fixed bed reactor, and the mixture of hydrogen peroxide, olefin and optionally solvent is passed over this packing. In the case of olefins which are gaseous under the reaction conditions, gaseous olefin and optionally additionally an inert gas are preferably fed in, the gaseous olefin or olefin-gas mixture preferably being passed cocurrent or countercurrent, preferably countercurrent, to the liquid mixture. The gaseous olefin or olefin-gas mixture in this case is preferably passed through the reactor, which is operated as a bubble column, from the bottom upwards, so that the gas stream is dispersed in the form of bubbles in the solution flowing countercurrent to the liquid mixture. The amount of the gas stream is chosen such that unreacted, gaseous olefin or, in the case of complete conversion, the inert gas is removed at the end of the reactor and the molecular oxygen formed in the reactor by decomposition of hydrogen peroxide is discharged from the reactor with this gas stream.

If the catalyst is employed in the form of a bed or packing, it can moreover be conditioned before the start of the epoxidation reaction, by bringing water, optionally mixed with a solvent and/or hydrogen peroxide, to a constant pH by addition of a base and passing it over the catalyst.

The abovementioned bubble procedure is suitable both for epoxidation according to the invention under pH control and for other processes of the generic type, for example those in which the catalyst is neutralized or in which selectivity-reducing acid functions of the catalyst are neutralized by chemical reaction.

The process according to the invention renders a continuous operating procedure possible, without the selectivity and yield ($H_2O_2$ conversion) being adversely influenced by variations in quality in the starting substances. Due to the separate metering of a base under pH control during the epoxidation in accordance with the invention, treatment of the catalyst before or during the epoxidation is unnecessary.

DETAILED DESCRIPTION OF THE PREFERRED EMBODIMENTS

EXAMPLES

Titanium silicalite granules prepared by the process described in Example 3 of EP 0 893 158, are used as the catalyst for all the examples. The propylene oxide selectivities (PO selectivity) stated were calculated as the ratio of the concentration of propylene oxide to the sum of the concentrations of the products propylene oxide, 1-methoxypropanol, 2-methoxypropanol and 1,2-propanediol.

Example 1 (Comparative Example)

300 g methanol are initially introduced into a thermostatically controlled laboratory autoclave equipped with a gas dispensing stirrer at 60° C. under a propylene atmosphere and are saturated with propylene under an excess pressure of 5 bar. A mixture of 518 g of 50.7 wt. % hydrogen peroxide (distilled), 2586 g methanol, 125 g MTBE (methyl tert-butyl ether), 253 g water and 10 g titanium silicalite is then metered in at a rate of 290 g/h, while stirring. At the same time, reaction mixture is removed via a valve in an amount such that the weight of the contents of the reactor remain constant. During the metering, propylene is supplemented via a pressure regulator in order to keep the pressure in the reactor constant. At regular intervals, the hydrogen peroxide content in the reaction mixture removed is determined by redox titration and the content of propylene oxide, 1-methoxy-2-propanol, 2-methoxy-1-propanol and 1,2-propanediol is determined by gas chromatography (GC). After 4 h, a stationary operating state is reached. Table 1 shows the hydrogen peroxide conversion and the propylene oxide selectivity in the stationary operating state.

For the hydrogen peroxide employed, a pH of 2.8 was measured with a combined glass electrode with integrated Ag/AgCl reference electrode. Corrected for the concentration potential of 50.7 wt. % hydrogen peroxide, an actual pH of 4.6 results.

Examples 2 to 5

Example 1 is repeated, with the difference that the hydrogen peroxide employed is brought to the pH shown in Table 1 by addition of 1N sodium hydroxide solution, the pH being measured with a combined glass electrode with integrated Ag/AgCl reference electrode. After 4.5 h, a stationary operating state with the hydrogen peroxide conversion and the propylene oxide selectivity shown in Table 1 is reached.

TABLE 1

| Example* | pH of the $H_2O_2$ | $H_2O_2$ conversion | PO selectivity |
| --- | --- | --- | --- |
| 1 | 2.8 | 71.0% | 54.9% |
| 2 | 4.0 | 71.4% | 60.7% |
| 3 | 4.5 | 69.5% | 77.1% |
| 4 | 4.75 | 65.3% | 85.2% |
| 5 | 5.0 | 35.3% | 94.2% |

Example 6 (Comparative Example)

Example 1 is repeated with the difference that sodium nitrate is added to the hydrogen peroxide employed in an amount such that it has the same sodium concentration as the hydrogen peroxide employed in Example 4 brought to pH 4.75 with sodium hydroxide solution. After 4.5 h, a stationary operating state with a hydrogen peroxide conversion of 69.6% and a propylene oxide selectivity of 68.0% is reached.

Example 7 (Comparative Example)

Example 1 is repeated, with the difference that a different titanium silicalite catalyst is used, the reaction temperature is 65° C. and a mixture of 708 g of 43.1 wt. % hydrogen peroxide (crude product from the anthraquinone process), 1743 g methanol, 51 g MTBE and 35 g titanium silicalite is metered in at a rate of 200 g/h. After 4.5 h, a stationary operating state is reached. Table 2 shows the hydrogen peroxide conversion and the propylene oxide selectivity in the stationary operating state.

Examples 8 to 11

Example 7 is repeated, with the difference that the hydrogen peroxide employed is brought to the pH shown in Table 2 by addition of 25 wt. % aqueous ammonia, the pH being measured with a combined glass electrode with integrated Ag/AgCl reference electrode. After 4 to 5.5 h, a stationary operating state with the hydrogen peroxide conversion and the propylene oxide selectivity from Table 2 is reached.

TABLE 2

| Example | pH of the $H_2O_2$ | $H_2O_2$ conversion | PO selectivity |
| --- | --- | --- | --- |
| 7 | 2.42 | 58.5% | 66.8% |
| 8 | 5.15 | 53.2% | 88.5% |
| 9 | 5.35 | 50.5% | 92.1% |
| 10 | 5.55 | 41.2% | 92.2% |
| 11 | 5.75 | 27.1% | 92.7% |

Examples 12 to 15

Example 7 is repeated, with the difference that the mixture of hydrogen peroxide, methanol and MTBE employed is brought to the pH shown in Table 3 by addition of 25 wt. % aqueous ammonia before the addition of the catalyst, the pH being measured with a combined glass electrode with integrated Ag/AgCl reference electrode. After 4 to 5.5 h, a stationary operating state with the hydrogen peroxide conversion and the propylene oxide selectivity from Table 3 is reached.

TABLE 3

| Example | pH of the $H_2O_2$/MeOH mixture | $H_2O_2$ conversion | PO selectivity |
| --- | --- | --- | --- |
| 7 | 4.39 | 58.5% | 66.8% |
| 12 | 5.46 | 58.3% | 78.4% |
| 13 | 6.81 | 58.9% | 80.6% |
| 14 | 7.22 | 57.1% | 81.7% |
| 15 | 7.69 | 56.3% | 86.7% |
| 8 | 8.12 | 53.2% | 88.5% |
| 10 | 8.23 | 41.2% | 92.2% |
| 11 | 8.66 | 27.1% | 92.7% |

Examples 16 to 19

65.7 g titanium silicalite catalyst in the form of extrudates of 2 mm diameter are initially introduced into a thermostatically controlled tubular reactor. A mixture of 278 g of 42.9 wt. % hydrogen peroxide, 6672 g methanol and 51 g MTBE is brought to the pH shown in Table 4 with 25 wt. % aqueous ammonia and then saturated with propylene under an excess pressure of 3 bar at 45° C. This mixture is then passed over the catalyst at 39° C. at a rate of 900 g/h. At regular intervals, the hydrogen peroxide content in the resulting reaction mixture is determined by redox titration and the content of propylene oxide, 1-methoxy-2-propanol, 2-methoxy-1-propanol and 1,2-propanediol is determined by GC. After operation for 8 h, the hydrogen peroxide conversion and propylene oxide selectivity shown in Table 4 are reached.

TABLE 4

| Example | pH of the $H_2O_2$/MeOH mixture | $H_2O_2$ conversion | PO selectivity |
| --- | --- | --- | --- |
| 16 | 5.5 | 94.9% | 62.3% |
| 17 | 8.5 | 74.3% | 78.6% |
| 18 | 8.7 | 65.9% | 86.6% |
| 19 | 8.9 | 56.1% | 92.4% |

Example 20 (Comparative Example)

68.0 g titanium silicalite catalyst in the form of extrudates of 2 mm diameter are initially introduced into a thermostatically controlled tubular reactor. A mixture of 1334 g 42.9 wt. % hydrogen peroxide, 6600 g methanol and 67 g MTBE is fed in at the lower end of the reactor at 50° C. at a rate of 600 g/h. At the same time, 200 g/h gaseous propylene are added at the lower end of the reactor. The liquid reaction mixture and unreacted, gaseous propene in an amount such that an excess pressure of 15 bar is maintained are removed at the upper end of the reactor. At regular intervals, the hydrogen peroxide content of the reaction mixture removed is determined by redox titration and the content of propylene oxide, 1-methoxy-2-propanol, 2-methoxy-1-propanol and 1,2-propanediol is determined by GC. After operation for 8 h, the hydrogen peroxide conversion and propylene oxide selectivity shown in Table 5 is reached.

Examples 21 to 23

Example 20 is repeated, with the difference that the mixture of hydrogen peroxide, methanol and MTBE employed is brought to the pH shown in Table 5 by addition of 25 wt. % aqueous ammonia, the pH being measured with a combined glass electrode with integrated Ag/AgCl reference electrode. After operation for 8 h, the hydrogen peroxide conversion and propylene oxide selectivity shown in Table 5 are reached.

TABLE 5

| Example | pH of the $H_2O_2$/MeOH mixture | $H_2O_2$ conversion | PO selectivity |
| --- | --- | --- | --- |
| 20 | 4.8 | 96.9% | 81.7% |
| 21 | 8.0 | 96.5% | 87.2% |
| 22 | 8.5 | 93.5% | 94.8% |
| 23 | 9.0 | 90.0% | 94.6% |

What is claimed is:

1. A process for the epoxidation of propene in the presence of a titanium silicalite catalyst, said process comprising:
   (a) introducing one or more solutions containing hydrogen peroxide and a propene compound as starting substances into an expoxidation reactor;
   (b) introducing a base into said epoxidation- reactor as a mixture with at least one of said starting substances; and
   (c) maintaining the pH in the mixture of said base and at least one of said starting substances so that it is between 4 and 9.5.

2. The process of claim 1, wherein said base is added to an aqueous hydrogen peroxide solution and the pH of said solution is established and kept at between 4 and 6.5 based upon measurements made by means of a glass electrode.

3. The process of claim 1, wherein said base is added to an aqueous-organic hydrogen peroxide solution with at least 50 wt. % of an organic water-soluble solvent and the pH of said solution is established and kept in the range of 5 to 9.5 based upon measurements made by means of a glass electrode.

4. The process of claim 1, wherein epoxidation is carried out in the presence of at least one organic solvent selected from the group consisting of: lower alcohols; and ethers; and wherein the weight ratio of hydrogen peroxide to organic solvent is in the range of 1:1 to 1:20.

5. The process of claim 1, wherein said base is selected from the group consisting of: alkali metal hydroxides; alkali metal carbonates; alkali metal bicarbonates; alkali metal phosphates; alkali metal carboxylates and ammonia.

6. The process of claim 1, wherein epoxidation is carried out in a fixed bed reactor filled with said titanium silicalite catalyst and wherein said starting substances are passed through said fixed bed reactor in a cocurrent or countercurrent flow.

7. The process of claim 1, wherein said propene is epoxidized at a molar ratio of propylene to hydrogen peroxide in a range equal to or greater than 1 to 10, said epoxidation being carried out in the presence of methanol, at a temperature in the range of from 20° to 70° C. and under a propene pressure in the range of from 0.1 to 1.0 MPa.

8. The process of claim 1, wherein propene is epoxidized in a fixed bed reactor operating as a bubble column and wherein said propene is dispersed in solution by countercurrent flow.

* * * * *